United States Patent [19]

Bengmark et al.

[11] Patent Number: 5,474,932
[45] Date of Patent: Dec. 12, 1995

[54] INTESTINE COLONIZING STRAINS OF LACTOBACILLI

[75] Inventors: Stig Bengmark, Lund; Siv Ahrné, Bjärred; Göran Molin; Bengt Jeppson, both of Lund, all of Sweden

[73] Assignee: Probi AB, Lund, Sweden

[21] Appl. No.: 989,030

[22] PCT Filed: Jul. 24, 1992

[86] PCT No.: PCT/SE92/00528

§ 371 Date: Apr. 16, 1993

§ 102(e) Date: Apr. 16, 1993

[87] PCT Pub. No.: WO93/01823

PCT Pub. Date: Feb. 4, 1993

[30] Foreign Application Priority Data

Jul. 25, 1991 [SE] Sweden .................................. 9102238

[51] Int. Cl.[6] .................................................. C12N 1/20
[52] U.S. Cl. .................. 435/252.9; 435/853; 435/856; 435/857; 424/93.45
[58] Field of Search ................... 424/93 C, 93 J, 424/93 D; 426/2; 435/853, 856, 857, 252.9

[56] References Cited

FOREIGN PATENT DOCUMENTS

| 0199535 | 10/1986 | European Pat. Off. . |
| 0271364 | 6/1988 | European Pat. Off. . |
| 89 05849 | 6/1989 | WIPO . |
| 89 08405 | 9/1989 | WIPO . |
| 91 05851 | 5/1991 | WIPO . |
| 91 05850 | 5/1991 | WIPO . |

OTHER PUBLICATIONS

Savage, Prog. Food Natr. Sci 7(3–4):65–74 1983 Abstract Medline 84096420.
International Journal of Systematic Bacteriology, vol. 40, No. 2, Apr. 1990, Marie Stahl,. et al., "Restriction Endonuclease Patterns and Multivariate Analysis as a Classification Tool for Lactobacillus spp.", pp. 189–192.
System, Appl. Microbiol., vol. 11, 1989, Siv Ahrne, et al., "Plasmids in Lactobacillus Strains Isolated Form Meat and Meat Products", 320–324.
Scand J. Infect Dis, vol. 4, 1987, Ann Lidbeck, et al., "Impact of Lactobacillus Acidophilus Supplements on the Human Oropharyngeal and Intestinal Microflora", pp. 1–7.

*Primary Examiner*—Marian C. Knode
*Assistant Examiner*—Jean C. Witz
*Attorney, Agent, or Firm*—Oblon, Spivak, McClelland, Maier, & Neustadt

[57] ABSTRACT

A process for isolation of a strain of Lactobacillus having the ability of being established on human intestinal mucosa in vivo and being able to remain therein after oral administration for at least 10 days after the completion of the administration.

By the process the new strains *L. plantarum* 299 (DSM 6595) and *L. casei* ssp. *rhamnosus* 271 (DSM 6594) have been isolated, which are useful for the prophylaxis or treatment of bacterial infections, especially in the form of a fermented nutrient composition.

3 Claims, 3 Drawing Sheets

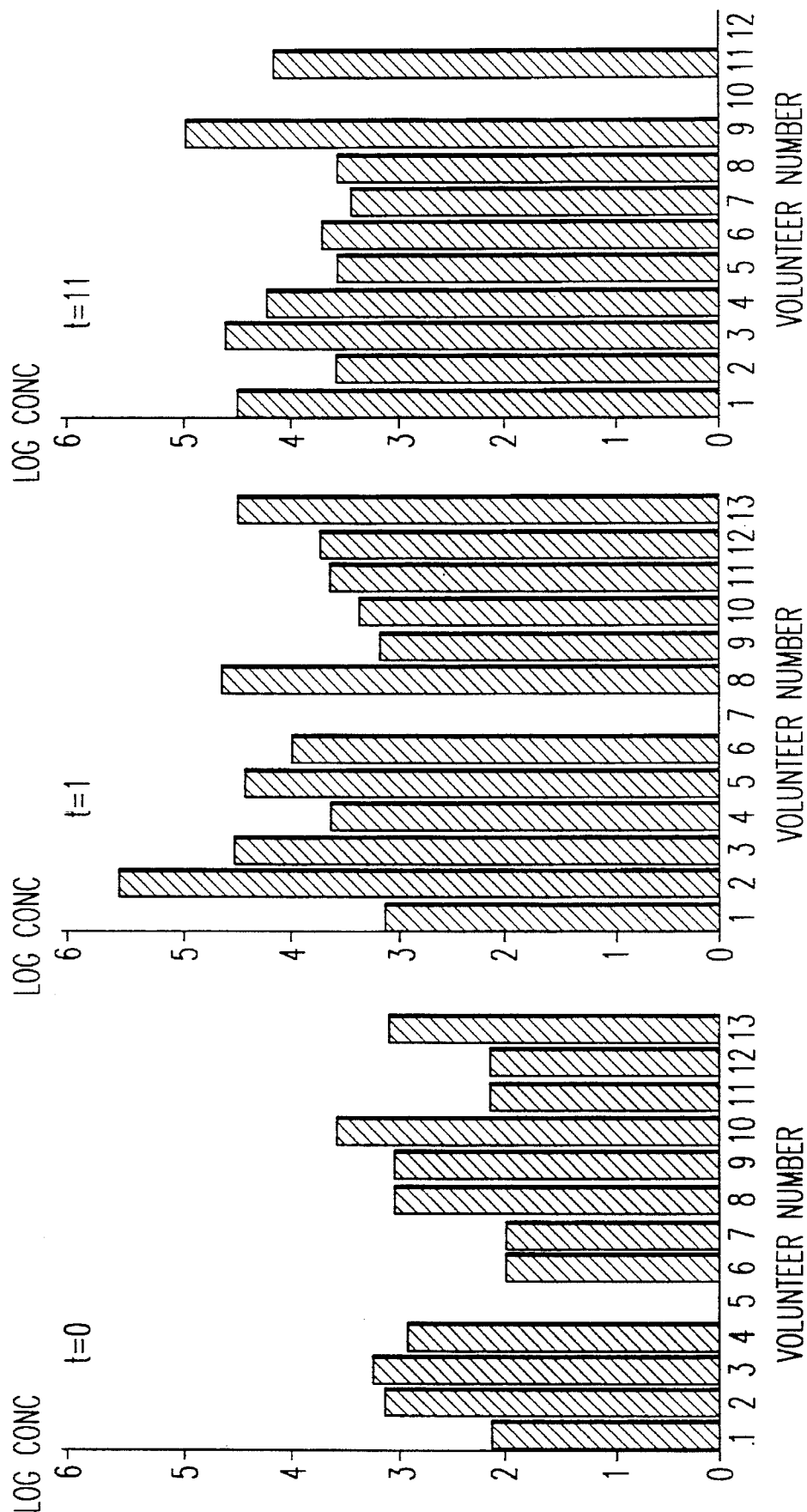

INTESTINE COLONIZING STRAINS OF LACTOBACILLI

This application is a 371 of PCT/SE92/00528, filed Jul. 24, 1992.

The present invention refers to a process for isolation of strains of Lactobacillus having the ability to colonize and become established on intestinal mucosa in vivo after oral administration, strains obtained by this process, and the use thereof for the prophylaxis or treatment of bacterial infections, especially in the form of a composition comprising an oatmeal based nutrient solution fermented by one of said strains.

Many people have a disturbed intestinal microflora, that is, the balance between useful and harmful intestinal bacteria is disturbed. A number of factors, among others stress, the occurence of bile salts, diet, etc. influence the bacterial flora. Most important is, however, that modern antibiotic treatment can destroy the normal flora for a long period of time, and thus, eliminate a normal fermentation process. Should the fermentation process be disturbed and the number of useful bacteria be reduced, the consequence will be that the colon mucosa withers away and ceases to function at the same time as the potentially malignant bacteria rapidly grow in number. These bacteria penetrate the malfunctioning colon wall and infect the organs of the body which leads to the so called intensive-care-disease with pus foci all over the body and possibly also an abolished function of most of the organs of the body, a collapse of organs. Blood poisoning, sepsis, caused by abscesses in the abdominal cavity is still a very common surgical complication in connection with abdominal surgery with a high death-rate. These patients are today treated by administration of antibiotics and surgical treatment of the abscess to the extent it could be located. At present antibiotics are conventionally administered before intestinal surgery in order to reduce the risk of post-operative infections and illness caused thereby. However, the treatment with antibiotics is expensive and moreover associated with a risk of different complications such as allergy and destruction of the normal intestinal flora and overgrowth with still more pathogenic bacteria.

The fact that lactobacilli should have a favourable effect on the intestinal mucosa is an old idea which has been brought up again. There are however many unclear points as to which microorganisms are involved and as to the ecology of the intestines. Another problem in this connection is that the classification of the genus Lactobacillus is incomplete which makes it difficult to identify those strains which are favourable to the function of the intestines. What, after all, seems to be commonly accepted today is that:

Bacteria of the genus Lactobacillus have a manifest ability of preventing the establishing of pathogenic bacteria in various ways, irrespective of foodstuffs or intestines being concerned;

Certain strains of Lactobacillus are more effective than other strains of the same species in protecting and activating the intestines;

Foodstuffs fermented by lactobacilli have proven to have a cholesterol reducing effect, probably because of a checking of the cholesterol production in the intestines, but maybe also because the bacteria use cholesterol for the production of steroids;

The consumption of great amounts of lactobacilli improves the intestinal motoric activity, the cause of this effect is unknown;

A large proportion of lactobacilli in the intestines counteracts cancer, something which seems to have several grounds. Firstly, certain lactobacilli are able to prevent the production of nitroseamines in the intestines by means of the enzyme nitritereductase; nitroseamines are cancerogenic. Secondly, lactobacilli may obstruct certain bacterially produced enzymes in the intestines from activating potentially carcinogenic substances. Finally, there are indications of lactobacilli having growth restricting effect on cancer rumours, maybe because the macrophages of the immunological defence system are activated by the presence of the lactobacilli.

A decisive weakness of the lactobacilli used today in most conventional foodstuffs is the poor survival of these organisms during the passage through the stomach and duodenum. This brought about a the development of a product called "acidofilusfil", acidophilus sourmilk, wherein milk was fermented with a strain of *Lactobacillus acidophilus* isolated directly from human faeces. *L. acidophilus* manages the passage through the upper part of the gastro-intestinal tract well. However, in order to have an effect on the microflora in the intestines for a longer period of time, it is essential that the lactobacillus is able to become established in the intestines. According to Lidbeck, A. et al, Scand J Infect Dis, 4, pp 531–537, 1987, the increase in the number of lactobacilli in the microflora of the intestines, which occurs after consumption of a preparation containing *Lactobacillus acidophilus*, is gradually slowing down as the consumption thereof ceases, and consequently after 9 days without supply the bacterial flora has regained its original composition.

EP-A2-0 199 535 describes a biologically pure culture of *Lactobacillus acidophilus*, ATCC accession No. 53 103, isolated from human faeces, being able to adhere to mucosal cells in tests in vitro. An adherence in vivo has, however, not been demonstrated.

WO 89/05849 describes lactic acid bacteria isolated from the gastro-intestinal tract in pigs and selected by means of, among others, adhesion to gastro-intestinal epithelial cells from pigs in vitro and tolerance against acid and bile. Said bacteria can be used for the fermentation of milk which then can be given to piglets to prevent or treat i.a. *E. coli* diarrhoea.

The strains of Lactobacillus which are commercially used today have above all been selected for being passably capable of growing in current primary products as for example milk. If a certain strain is to exercise an optional favourable influence, it is without doubt a prerequisite that it is able to become established in the intestines and to compete with the existing microflora. Knowledge about which properties are necessary for a certain Lactobacillus strain to be able to stand this competition is for the most part unknown.

The present invention refers to a process for isolaton of a strain of Lactobacillus having the ability to colonize and become established on human intestinal mucosa in vivo, characterized in that lactobacilli are isolated from human intestinal mucosa and are pure cultured in a suitable nutritient medium and then selected as to the ability to colonize and become established in the intestines.

The ability of the strain to colonize in the intestines is preferably tested by oral administration, and a subsequent verification of the occurence on the intestinal mucosa at least 10 days after the completion of the administration.

A complementary selection of isolated strains can take place, before or after the test of the colonization, by an evaluation of different functional and technical properties, such as bile resistance, pH-resistance, ability of fermentation of a requested substrate, preferably oatmeal, and of producing flavour, ability to resist freeze-drying, antibiotics resistance, etc.

To manage the passage through the gastro-intestinal tract the selected strains thus ought to be able to survive at a pH of 1.0 for 30 minutes and also to grow in the presence of 0.1% bile.

The invention also refers to strains of Lactobacillus having the ability of colonizing human intestinal mucosa in vivo, obtained by the isolation process described above. According to one theory the strains of Lactobacillus which are facultatively heterofermentative constitute a preferred type for the establishment in the intestines.

The invention especially refers to new Lactobacillus strains having the ability of colonizing human intestinal mucosa in vivo, which have been deposited according to the Budapest Agreement at the DSM—Deutsche Sammlung yon Mikroorganismen und Zellkulturen GmbH—, Braunschweig, Germany on Jul. 2, 1991, that is

| Lactobacillus plantarum 299 | DSM 6595 |
|---|---|
| Lactobacillus casei ssp. rhamnosus 271 | DSM 6594 |

The invention also refers to variants thereof having an essentially corresponding REA-pattern. A REA-pattern refers to the pattern formed in electrophoresis on agar gel of DNA which has been decomposed with a restriction enzyme according to the method described below. By characterization of the strains by means of their REA-pattern the identity of the used isolates can be established, something which has not been possible before. Closely related strains of Lactobacillus with differences in the REA-pattern show differences as to the ability of adherence to intestinal epithelium.

The invention also refers to a composition for the prophylaxis or treatment of infections in the gastro-intestinal tract, which comprises a Lactobacillus strain having the ability to colonize and become established in human intestinal mucosa in vivo, which has been obtained according to the method of the invention, combined with a conventional carrier.

In particular the invention refers to a composition comprising any of the strains

| Lactobacillus plantarum 299 | DSM 6595 |
|---|---|
| Lactobacillus casei ssp. rhamnosus 271 | DSM 6594 | or a variant thereof having an essentially corresponding REA-pattern.

Conventional carriers are for example physiologically acceptable substrates fermented by the bacterium in question, as well as foodstuffs of various kinds, especially based on starch or milk, but also inert solid or liquid substances, such as saline or water. A suitable substrate should contain liquid or solid fibres which are not resorbed in the gastro-intestinal tract and which when fermented with Lactobacillus form short fatty acids. As an example of suitable, starch-containing substrates can be mentioned cereals, such as oats and wheat, corn, root vegetables such as potatoes and certain fruits such as green bananas.

Modern medical care of patients in connection with illness and surgery is to a large extent based on the supply of nutrition via the veins, whereby the intestines are not supplied with material to ferment with subsequent consequences. The colon functions as the body's own fermentation tank, the purpose of which is to produce useful nutrients, among others for the function of the colon itself, but also for eliminating harmful substances, for example heavy metals, excessive amounts of cholesterol etc. In order for the colon to function there must be a supply of suitable bacteria and substrates, particularly starch and dietary fibres. About half of the contents of the colon is bacteria, mostly of the anaerobic type. The most important bacteria are those located on the colon mucosa. Among the bacteria of the colon there is a minority of a potentially harmful type. As long as the useful bacteria are present the harmful bacterial flora is suppressed. Recent studies have shown that the colon mucosa obtains most of its nutrition from fermentation products, mainly in the form of short fatty acids. A normal fermentation process requires a supply of about 30 g of dietary fibre daily and the presence of suitable bacteria.

A preferred substrate for the composition according to the invention, which also gives the composition an excellent nutritional value, is a nutrient solution based on oatmeal. The cereal oats has shown to be a good sustrate for fermentation in many ways: It is rich in proteins, carbohydrates, fat, dietary fibre and also water-soluble fibre, so called β-glucans. In addition oats or oatmeal fat has a very high content of surface-active phospholipids, which function as gastric mucosal barrier "corrosion inhibitors" and hence give mucosal protection. Finally, the amino acid composition of oat proteins corresponds to a large extent to the needs of the human body. In WO 89/08405 a nutrient composition is described suitable for enteral feeding, which is obtained by a combination of enzymatic decomposition of oatmeal with α-amylase, possibly protease, and β-glucanase and heat treatment and fermentation with a lactobacillus having the ability to adhere to the intestines spontaneously. The nutrient composition described in the referred patent application is in combination with a Lactobacillus strain according to the invention an excellent composition for nutrient administration to patients in connection with the normal treatment after large operations, for special treatment of patients being victims of the intensive-care-disease or an organ collapse, and for treatment of different intestinal diseases, for example ulcerative colitis.

To be useful in an oatmeal based nutrient composition according to the invention a Lactobacillus strain should fulfil the following conditions:

good fermentation of oats;

survival at a pH of 1.0 (which corresponds to the pH in the stomach) for 30 minutes;

survival and growth in the presence of bile salts;

ability of settling and remaining on the intestinal mucosa.

It is also essential that the pH-value during the fermentation is reduced quickly in order to stop the growth of other bacteria.

It has been shown that the administration of lactobacilli having the ability to colonize in or adhere to the intestines can suppress a different bacterial flora from colonizing the intestines and thus reduce the risk of sepsis in connection with bacterial infections such as complications following abdominal surgery. This treatment seems to be as efficient as the conventional treatment used today in the form of antibiotics. Hence, it seems to be reasonable that patients who are subjected to intestinal surgery are pretreated with lactobacilli rather than antibiotics. This means that a cheaper form of therapy could be established with less potential secondary effects as the normal intestinal flora would not be destroyed.

The invention also refers to the use of a nutrient composition fermented by a Lactobacillus strain in accordance with the invention instead of antibiotics for the prophylaxis or treatment of bacterial infections in connection with surgical operations, post surgical rehabilitation etc.

It especially refers to an oatmeal based nutrient solution fermented by *Lactobacillus plantarum* 299.

Experiments with test animals have shown a statistically valid survival in animals treated with a composition comprising a Lactobacillus strain isolated from the intestinal mucosa of an animal of the same species. Tests with rats have shown a good prevention and quicker healing of experimentally induced colitis (colit) and ulcers in the intestines.

The composition according to the invention can be administered in any suitable way, preferably orally or rectally, for example in the form of enema. It can also be administered enterally through a catheter inserted in the intestines via the stomach or directly in the intestines. Tests have shown that the effect is improved if dietary fibres in the form of for example oatmeal gruel or of β-glucans are supplied. The treatment should take place once or several times daily for a period of 1–2 weeks.

BRIEF DESCRIPTION OF THE DRAWINGS

On the enclosed drawings FIG. 3 shows the concentration of lactobacilli in ileum before, immediately after, and a few days after, respectively, oral administration of an oatmeal gruel fermented by Lactobacillus.

EXAMPLES

Isolation of Lactobacillus strains from humans

Figure 1:
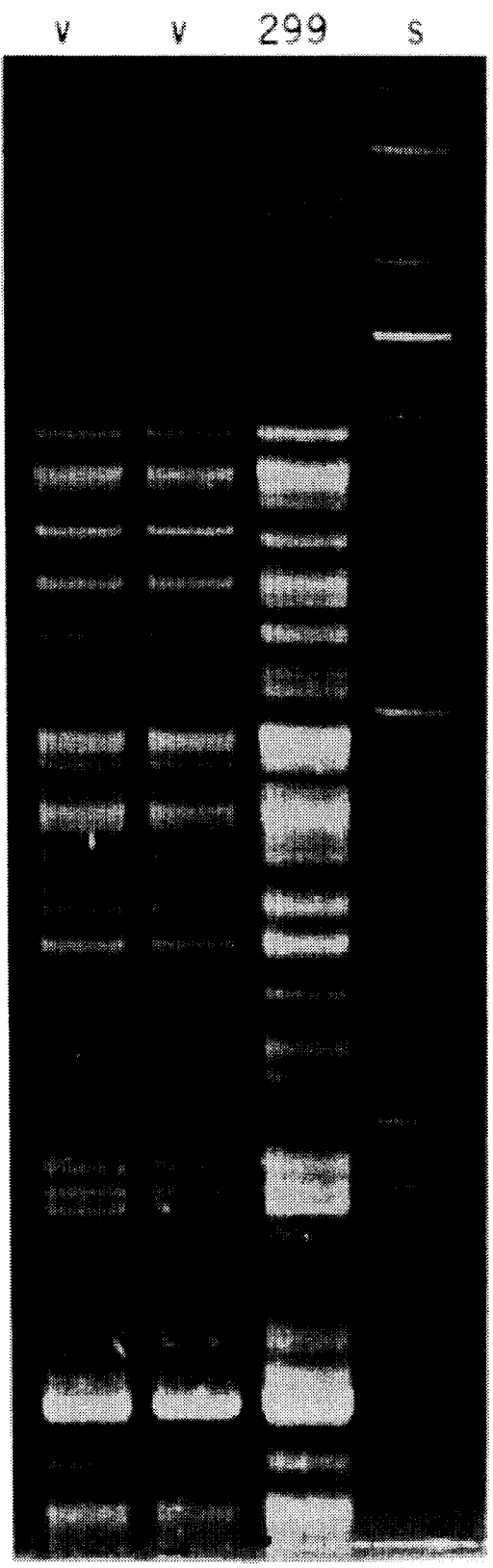
FIGS. 1–2 show the REA-pattern of the new Lactobacillus strains 299 and 271.

In order to isolate strains having the ability to colonize and become established on human intestinal mucosa, strains of Lactobacillus have been sampled from human mucosa. Biopsies from colon were taken by means of enteroscopy and pieces of the intestinal mucosa from the small intestine (jejunum and ileum) were removed in connection with surgical operations. The mucosa samples were immediately placed in a special medium (0.9% NaCl, 0.1% pepton, 0.1% Tween 80 and 0.02% cystine; all values refer to % by weight/volume), homogenized in ultrasonic baths for 2 minutes and stirred for 1 minute before being placed on Rogosa agar (Difco Laboratories, Detroit, Mich., U.S.A.). The plates were incubated anaerobically at 37° C. for 2 d (Gas Pak Anaerobic System, BBL). One to three colonies were picked at random from each plate and were grown in pure cultures 5 to 9 times on Rogosa agar and kept as dense cultures in a frozen buffer at −80° C. A total of 209 Lactobacillus strains were isolated from about 61 different subjects. All isolates were characterized as to the ability of fermenting 49 different carbohydrates by means of API 50 CH, a commercial test kit from API, Montalieu Verceu, France. No significant difference in the composition of the lactobacilli flora between the small and the large intestines could be found.

Representative strains from the different groups were evaluated as to pH-resistance, ability of growing in the presence of bile, and ability of fermenting oatmeal gruel.

The pH-resistance was tested by adding 0.1 ml bacterial suspension ($10^9$ CFU/ml which had been cultivated in Rogosa broth, centrifuged and resuspended in a physiological salt solution) to 2 ml phosphate buffer at pH 1.0. After 30 minutes Rogosa agar plates were inoculated and if any growth was visible after incubation at 37° C. for 3 days the test was considered to be positive. Only a few of the tested strains passed this test.

Growth in the presence of bile was tested by growing isolates of Lactobacillus in the presence of 0.1% and 0.15%, respectively, beef bile in Rogosa agar plates incubated anaerobically for 3 days at 37° C. About 80% of the strains were able to grow in the presence of 0.1% bile, whereas only 18% managed to grow in 0.15% bile.

Based on the results of these tests 20 different Lactobacillus strains were selected for further investigation.

Intestinal colonization in vivo in humans

Healthy test subjects were for a certain period of time daily given a fermented oatmeal gruel comprising a mixture of twenty different strains of Lactobacillus, carefully selected in accordance with the above. It was then investigated which of the consumed strains could be found on the mucosa from the small and large intestine.

Fermented oatmeal gruel was made according to the protocol described below. This was done with each of the strains of Lactobacillus in the study, as stated in Table 1 below. The different preparations were mixed in such proportions that the final product contained $8 \times 10^7$ CFU per gram freeze-dried product.

In the study 12 volunteers aged between 31 and 56 years participated, each of which received ten bottles of 100 ml liquid oatmeal gruel based on 1 g freeze-dried product per ml water. Samples from the intestinal mucosa were taken before the consumption of the oatmeal gruel had started, after 11 days when the subjects had consumed 100 ml oatmeal gruel for breakfast daily for a period of 10 days, and after another 10 days, that is 11 days after the completion of the oatmeal gruel consumption. The intestinal samples were taken as biopsies from the small intestine (ileum) by means of a Watson capsule, and from rectum with a rectoscope. The biopsies were prepared as described above and analysed as to the contents of viable Lactobacillus. From each sample about ten colonies were picked from the Rogosa agar plate, which were grown in pure cultures and freeze-stored at −80° C. until they were identified.

All isolates were tested on API 50 CH as above. The isolates that seemed to correspond with or mainly correspond with any of the test strains were tested further by plasmid analysis and restriction endonuclease analysis according to the methods described below.

As a general trend it was observed that the content of lactobacilli on the intestinal mucosa was increased during the consumption of fermented oatmeal gruel and that this increase was continued for 11 days after the completion of the administration. In FIG. 3 the logarithmic concentration of lactobacilli in ileum is shown by means of a column diagram before the start of the test (t=0), on the day after the completion of the test (t=1) and after another 10 days (t=11). The increase was more pronounced in the small intestine, but on the other hand the content of lactobacilli as a whole was larger in the large intestine. Furthermore, it could be noted that the contents of Gram negative anaerobic bacteria in the colon were reduced after the consumption of the fermented oatmeal gruel.

The following strains were found in a dominating position on the intestinal mucosa 10 days after the completion of the administration of lactobacilli:

*Lactobacillus plantarum* 299 was found in 11 subjects (in 5 subjects only on the small intestine and in 5 others only on the large intestine);

*Lactobacillus casei* ssp. *rhamnosus* 271 was found in 4 subjects (in 1 only on the small intestine and in 2 others only on the large intestine);

*Lactobacillus reuteri* 108 was found in 4 subjects (in 1 only on the small intestine and in 1 other only on the large intestine);

*Lactobacillus murinus/casei* ssp. tolerance 294 was found in 2 subjects.

The strains which were reisolated 11 days after the completed administration were found on the mucosa in an approximate concentration of $3\times10^3$ to $10^5$ CFU/g mucosa for the small intestine and a concentration of $10^3$ to $3\times10^7$ CFU/g mucosa for the large intestine.

Preparation of oatmeal gruel

Fermented oatmeal gruel was made in three steps:

(i) 1295 g oatmeal (MP-450, Nord-Mills, Järna; protein content 14.2% and ash content 2.1%), 129.5 g enzyme mixture (Nord Malt, Söderhamn) and 5390 g tap water were mixed and heated to 95° C. during slow stirring. The gruel was cooled to 50° C., 1% β-glucanase (weight/volume) was added (GV-L; Grindsted Products A/S, Braband, Denmark) and then was incubated for 2 hours at 50° C.;

(ii) The gruel was inoculated with fresh lactobacilli and fermented at 37° C. for 15–20 hours. The pH was 3.4 to 3.9. The fermentation was carried out with the different strains each separately and the number of colony forming units, CFU, per ml product varied between $6\times10^6$ and $2\times10^8$ on Rogosa agar (anaerobically at 37° C. for 20 hours);

(iii) The fermented gruel was freeze-dried. The different products were mixed in such a proportion that the same value of CFU/g was obtained for all the strains. The mixture was supplemented with 20% (w/w) soybean flour (protein 51%, ash content 5.5%, fat 1%). The enriched mixture contained $2\times10^7$ CFU/g and was kept at −18° C. Non-fermented oatmeal gruel was made in the same way as above, but without fermentation.

Oatmeal gruel was made with all the 20 strains which had been selected for the intestine colonization test described above and was evaluated as to the concentration before and after freeze-drying and as to flavour. The results are given in Table 1 below.

TABLE 1

Selected strains of Lactobacillus for clinical tests

| Strain No. | Description | CFU/g | CFU*/g | Flavour*** |
|---|---|---|---|---|
| 138 | "aggregating" | $8,8 \times 10^8$ | $1,78 \times 10^8$ | 1 |
| 132 | L. salivarius | $1,1 \times 10^9$ | $6,5 \times 10^6$ | 3 |
| 47 | L. reuteri | $1,2 \times 10^9$ | $3,7 \times 10^7$ | 1 |
| 108 | L. reuteri | $1,5 \times 10^9$ | $1,88 \times 10^7$ | 1 |
| 98 | L. casei pseudo-plantarum | $1,63 \times 10^9$ | $6,6 \times 10^8$ | 2 |
| 292 | L. gasseri | $1,58 \times 10^9$ | $5,1 \times 10^8$ | 4 |
| 299 | L. plantarum | $1,92 \times 10^9$ | $6,71 \times 10^8$ | 5 |
| 136 | L. casei casei | $3,5 \times 10^9$ | $1,48 \times 10^9$ | 2 |
| A1 | L. plantarum | $2,27 \times 10^9$ | $4,15 \times 10^8$ | 5 |
| 271 | L. casei rhamnosus | $4,3 \times 10^9$ | $6,10 \times 10^8$ | 4 |
| 227 | L. buchneri | $9,45 \times 10$ | $1,81 \times 10^8$ | 1 |
| 140 | L. gasseri | $1,2 \times 10^8$ | $8,5 \times 10^6$ | 4 |
| 294 | L. murinus/casei tolerance | $1,63 \times 10^9$ | $1,3 \times 10^8$ | 3 |
| 283 | L. plantarum | $7,43 \times 10^8$ | $7,55 \times 10^7$ | 4 |
| 282 | cluster 25** | $7,8 \times 10^8$ | $6,65 \times 10^7$ | 2 |
| 96 | cluster 19** | $4,9 \times 10^8$ | $4,3 \times 10^7$ | 3 |
| 99 | cluster 12** | $4,6 \times 10^9$ | $1,39 \times 10^9$ | 4 |

TABLE 1-continued

Selected strains of Lactobacillus for clinical tests

| Strain No. | Description | CFU/g | CFU*/g | Flavour*** |
|---|---|---|---|---|
| 99* | cluster 12** | $1,0 \times 10^9$ | $1,6 \times 10^8$ | 2 |
| 308 | L. acidophilus | $5,9 \times 10^8$ | $1,0 \times 10^8$ | 3 |
| 280 | L. salivarius | $3,0 \times 10^8$ | $2,43 \times 10^6$ | 3 |

*after freeze-drying
**the cluster-numbering refers to a work in numerical taxonomy on intestine associated *lactobacilli* by Molin G et al (under publication).
***on a scale 5-1

The ability of giving the oatmeal gruel a pleasant flavour by the fermentation was judged by an "expert panel" consisting of four persons who judged the oatmeal gruels fermented by different strains. The flavour was estimated in a dropping scale from 5 to 1, where 5 denotes the judgement "very good" and 1 the judgement "unsavoury". The values for the 20 selected test strains are shown in Table 1 above.

Fermentation of oatmeal gruel

The four strains which were found on the intestinal mucosa in a dominating amount were investigated further as to the ability to ferment oatmeal gruel, the ability to resist freeze-drying and as to the development of flavour in oatmeal gruel.

The ability of fermenting oatmeal gruel was judged by means of the ability to reduce pH below 4.0 and form CFU at a level of $>10^8$ CFU/g wet weight.

The ability of resisting freeze-drying in oatmeal gruel was another selection criterium. In this connection the CFU concentration was measured after freeze-drying.

The result of the test above with oatmeal gruel is shown in table 2 below.

TABLE 2

Fermentation of oatmeal gruel with selected strains of Lactobacillus

| | Strain 299 | 271 | 294 | 108 |
|---|---|---|---|---|
| final pH | 3.6 | 3.8 | 3.4 | 3.8 |
| acid value | 8.0 | 6.5 | 8.1 | 6.5 |
| L-lactate, g/100 g | 0.18 | 0.40 | 0.32 | 0.25 |
| D-lactate, g/100 g | 0.390 | 0.031 | 0.24 | 0.19 |
| lactate tot., g/100 g | 0.57 | 0.43 | 0.55 | 0.44 |
| D-lactate in % | 69 | 7 | 43 | 44 |
| acetate, g/100 g | 0.0084 | 0.013 | 0.13 | 0.0026 |
| reduction after freeze-drying in % | 65 | 86 | 94 | 98 |
| final CFU/g | $2 \times 10^9$ | $4 \times 10^9$ | $8 \times 10^8$ | $1 \times 10^9$ |

In addition the flavour of the selected 4 strains was evaluated in comparision with on one hand a commercial youghurt culture (*Streptococcus thermophilus* and *Lactobacillus bulgaricus*) and on the other hand a commercial culture of acidophilus sourmilk (*Lactobacillus acidophilus*) using the same evaluation symbols as above. The results are given in Table 3 below.

TABLE 3

Flavour of oatmeal gruel fermented with strains of Lactobacillus

| Yoghourt | Acidophilus sourmilk | 299 | 271 | 294 | 108 |
|---|---|---|---|---|---|
| 3 | 2 | 5 | 4 | 3 | 1 |

On the basis of these values the strains 299 and 271 were judged to be of special interest and are described in further detail below.

Description of Lactobacillus strains 299 and 271

The strains 299 and 271, which were both isolated from healthy human intestinal mucosa, have been deposited at the Deutsche Sammlung von Mikroorganismen und Zellkulturen GmbH on Jul. 2, 1991 and have been given the deposition numbers DSM 6595 (299) and DSM 6594 (271).

Phenotype description

The strains 299 and 271 are Gram positive, catalase negative rods growing on Rogosa agar at pH 5.5. The capacity of the strains to ferment different carbohydrates is shown in Table 4. The tests have been carried out by means of the API 50 CH in accordance with the instructions of the manufacturer.

TABLE 4

Ability to form acid from different carbohydrates

| | | Strains | |
|---|---|---|---|
| | | 299 | 271 |
| 1. | Glycerol | − | − |
| 2. | Erythrithol | − | − |
| 3. | D-arabinose | − | − |
| 4. | L-arabinose | + | − |
| 5. | Ribose | + | + |
| 6. | D-xylose | − | − |
| 7. | L-xylose | − | − |
| 8. | Adonithol | − | − |
| 9. | β-methyl-xyloside | − | − |
| 10. | Galactose | + | + |
| 11. | D-glucose | + | + |
| 12. | D-fructose | + | + |
| 13. | D-mannose | + | + |
| 14. | L-sorbose | − | + |
| 15. | Rhamnos | − | + |
| 16. | Dulcitol | − | − |
| 17. | Inositol | − | + |
| 18. | Mannitol | + | + |
| 19. | Sorbitol | + | + |
| 20. | α-methyl-D-mannoside | + | + |
| 21. | α-methyl-D-glucoside | − | + |
| 22. | N-acetyl-glucosamine | + | + |
| 23. | Amygdalin | + | + |
| 24. | Arbutin | + | + |
| 25. | Esculin | + | + |
| 26. | Salicin | + | + |
| 27. | Cellobiose | + | + |
| 28. | Maltose | + | + |
| 29. | Lactose | + | + |
| 30. | Melibiose | + | − |
| 31. | Saccharose | + | + |
| 32. | Trehalose | + | + |
| 33. | Inulin | − | − |
| 34. | Melezitose | + | + |
| 35. | D-raffinose | − | − |
| 36. | Amidon | − | − |
| 37. | Glycogene | − | − |
| 38. | Zylitol | − | − |
| 39. | β-gentiobiose | + | + |
| 40. | D-turanose | + | + |
| 41. | D-lyxose | − | + |
| 42. | D-tagatose | − | + |
| 43. | D-fucose | − | − |
| 44. | L-fucose | − | − |
| 45. | D-arabitol | − | − |
| 46. | L-arabitol | − | − |
| 47. | Gluconate | + | + |
| 48. | 2-keto-gluconate | − | − |
| 49. | 5-keto-gluconate | − | − |

Phenotypically strain 299 can be identified as *Lactobacillus plantarum* (only raffinose deviated from the test pattern for *L. plantarum* ATCC 14917T; this is the type strain for the species *L. plantarum*, that is the strain which defines the species). 271 can be identified as *Lactobacillus casei* subsp. *rhamnosus* (corresponds completely to the type strain for the species).

Genotype description

The two strains have been examined as to the cleavage pattern of the chromosome DNA in connection with cleavage with EcoRI, through restriction-endonuclease analysis—REA—(method according to Ståhl M., Molin G., Persson A., Ahrné S. & Ståhl S., International Journal of Systematic Bacteriology, 40:189–193, 1990). Schematically REA can be described as follows:

(1) Chromosome DNA is isolated from the strains involved in the study;

(2) The DNA is cleaved with restriction enzymes;

(3) The cleaved DNA fragments are separated as to size by agarose gel electrophoresis;

(4) The band patterns of the different strains are registered and interpreted by means of a laser densitometer and associated programs. The differences between the strains regarding the REA-pattern can be expressed mathematically by means of principal component analysis. 1990).

Furthermore an examination has been carried out referring to the contents of plasmids (method according to Ahrné S., Molin G. & Ståhl S., Systematic and Applied Microbiology 11:320–325, 1989).

Strain 299: This strain contains four plasmids which are of the sizes of 4 MDal, 9 MDal, 20 MDal and 35 MDal, respectively. The cleavage pattern of the chromosomal DNA is shown in FIG. 1. The lane marked with 299 shows the pattern of strain 299 and the lanes marked with a v represent a genetical variant of strain 299 from two different isolates; this variant was one of the 20 strains that were tested on humans and has in Table 1 been denoted as A1; lane s denotes the standard, High $M_w$ DNA Markers (AEH; BRL, Bethesda Research Laboratories, Life Technologies, Inc.). The variant of 299 can by means of common phenotype tests not be separated from 299. Also genetically 299 and 299v are very close. The variant has also proved to have the same ability to be established in human intestinal mucosa.

Figure 2:
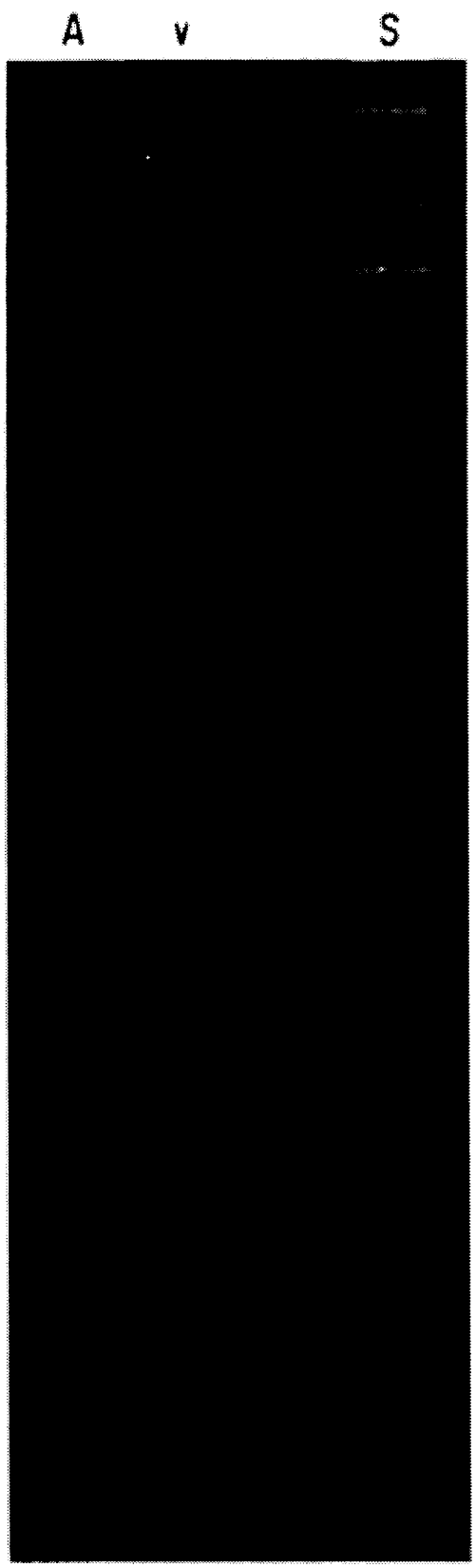

Strain 271: This strain contains two plasmids with a size of 3 MDal and 5 MDal, respectively. The cleavage pattern of the chromosomal DNA of the strain is shown in FIG. 2, as lane A; lane v shows a genetical variant of strain 271; and lane s denotes the same standard as in FIG. 1. The variant of 271 can with common phenotype tests not be separated from 271. Also genetically 271 and 271v are very close. The variant also has turned out to have the same ability to colonize the human intestinal mucosa as the sister strain.

Genetically the two examined strains differ essentially. They also differ significantly from the respective type strain.

Cultivation of Lactobacillus 299

An inoculate from a freezer of −80° C. is added to 50 ml Lactobacillus Carrying Medium (LCM, Efthymiou & Hansen, J. Infect. Dis., 110:258–267, 1962) or Rogosa, is incubated for about 40 hours at 37° C., 50 ml is inoculated into 500 ml LCM, is incubated about 40 hours at 37° C., 500 ml is inoculated into 5 liters, is incubated about 25–30 hours at 37° C., is centrifuged at 10 000 rpm for 10 minutes, is washed once in a physiological salt solution, the pellet is dissolved in about 1 liter of physiological salt solution.

This amount is estimated to be sufficient for about 400–500 l of oatmeal gruel. Cultivation media are not optimized. Rogosa worked better than LCM, possibly due to a better buffer function. 2% glucose was added to LCM. The same procedure can be used for producing the other Lactobacillus strains.

Biological test on rat

Rats having a weight of 250–300 g were subjected to a standard operation to develop an abscess in the abdominal cavity by isolating and puncturing a part of the large intestine by which a constant leekage of intestinal contents out into the abdominal cavity was obtained which caused an abscess within 24 hours, sepsis and subsequent high rate of mortality. Three groups of 30 animals each were used. Group 1 was an untreated control group, Group 2 was treated with antibiotics, by injection, and Group 3 was supplied with lactobacilli in the form of a fermented oatmeal gruel to the stomach. The Lactobacillus strain which was used had been isolated from rat intestinal mucosa and in tests proved to be able to colonize and become established in rat intestines.

Evaluation of the test was made by analysis of the content of bacteria in the blood, something which is equivalent to sepsis, as well as cultures from the abdominal cavity and intestines. The result shows that all animals in Group 1 had bacteria in the blood, which should lead to a very high rate of mortality. In Groups 2 and 3 similar results were obtained with the occurrence of bacteria in 3 of 30 animals, however, to a much lesser extent than in Group 1.

We claim:

1. A biologically pure culture of a Lactobacillus strain having the ability to colonize human intestinal mucosa in vivo and having all the identifying characteristics of *Lactobacillus plantarum* 299 DSM 6595 or *Lactobacillus* ssp *rhamnosus* 271 DSM 6594.

2. The biologically pure culture of claim 1, wherein said strain is *Lactobacillus plantarum* 299 DSM 6595.

3. The biologically pure culture of claim 1, wherein said strain is *Lactobacillus* ssp *rhamnosus* 271 DSM 6594.

* * * * *